(12) United States Patent
Berdovich

(10) Patent No.: US 9,500,598 B2
(45) Date of Patent: Nov. 22, 2016

(54) CHALLENGE SETS AND METHODS OF MAKING AND USING THE SAME

(71) Applicant: MICRO MEASUREMENT LABORATORIES, INC., Wheeling, IL (US)

(72) Inventor: Dan Berdovich, Prospect Heights, IL (US)

(73) Assignee: MICRO MEASUREMENT LABORATORIES, INC., Wheeling, IL (US)

( * ) Notice: Subject to any disclaimer, the term of this patent is extended or adjusted under 35 U.S.C. 154(b) by 0 days.

(21) Appl. No.: 14/508,206

(22) Filed: Oct. 7, 2014

(65) Prior Publication Data

US 2015/0098080 A1 Apr. 9, 2015

Related U.S. Application Data

(60) Provisional application No. 61/887,641, filed on Oct. 7, 2013.

(51) Int. Cl.
*G01N 1/00* (2006.01)
*G01N 21/93* (2006.01)
*G01N 21/88* (2006.01)
(Continued)

(52) U.S. Cl.
CPC .......... *G01N 21/93* (2013.01); *G01N 21/8803* (2013.01); *G01N 21/9027* (2013.01); *G01N 2001/2893* (2013.01)

(58) Field of Classification Search
CPC ........ G01N 1/28; G01N 21/90; G01N 21/93; G01J 1/02
USPC ....... 356/335–343, 220, 238.3, 239.8, 240.1, 356/36–38, 246; 73/865.8
See application file for complete search history.

(56) References Cited

U.S. PATENT DOCUMENTS 4,136,930 A 1/1979 Gomm et al.
5,279,017 A 1/1994 Foreshew
(Continued)

FOREIGN PATENT DOCUMENTS

WO 2012/024650 A2 2/2012

OTHER PUBLICATIONS

International Search Report and Written Opinion issued in corresponding International Application No. PCT/US14/59430 on Jan. 9, 2015 (12 pages).

(Continued)

*Primary Examiner* — Hoa Pham
(74) *Attorney, Agent, or Firm* — Buchanan Ingersoll & Rooney PC

(57) ABSTRACT

A surrogate challenge set including a plurality of containers containing a fluid, wherein at least one of the containers contains particulate matter; and reference probability-of-detection (POD) data for the at least one container containing the particulate matter is described. The fluid may be water containing at least about 0.5 wt % of a preservative, such as benzyl alcohol. The containers may be pharmaceutically acceptable containers such as vials, bottles, syringes, ampules and intravenous bags. The particulate matter may consist of a single particle having a particle size of at least about 50 μm. A method of making the challenge set may include: disposing particulate matter in at least one of a plurality of containers comprising a fluid; generating probability-of-detection (POD) data for the plurality of containers; and including the probability-of-detection (POD) data in the challenge set. Methods of using the surrogate challenges sets are also provided.

30 Claims, 2 Drawing Sheets

(51) Int. Cl.
 *G01N 1/28* (2006.01)
 *G01N 21/90* (2006.01)

(56) References Cited

U.S. PATENT DOCUMENTS

| | | |
|---|---|---|
| 6,953,465 B2 | 10/2005 | Dieck et al. |
| 2005/0099625 A1* | 5/2005 | Budd ................. G01N 15/0205 356/335 |
| 2006/0072111 A1 | 4/2006 | Budd et al. |
| 2011/0252899 A1 | 10/2011 | Felts et al. |

OTHER PUBLICATIONS

Pharmacopeial Forum Online, First Supplement to USP 37-NF 32, Physical Tests/ <790> Visible Particulates in Injections, Aug. 1, 2014, pp. 6393-6395.

R. Cherris: "General Visual Inspection Bench Parameters," 2009-2013, Bridge Associates International.

European Medicines Agency (EMEA)Chapter 2.9.18 to 2.9.20; Jan. 2008:20920.

* cited by examiner

CHALLENGE SETS AND METHODS OF MAKING AND USING THE SAME

FIELD OF THE INVENTION

The present disclosure relates to surrogate challenge sets for inspection of drug products intended for injection or ophthalmic use. More specifically, the present disclosure relates to surrogate challenge sets that are provided with probability-of-detection (POD) data for each container of the surrogate challenge set. Also disclosed are methods of making and using the surrogate challenge sets described herein.

BACKGROUND

Inspection of pharmaceutical-type product in the operations area is primarily focused on container and closure defects and particulate matter in the product. Both types of defects present potential harm to a patient and the circumstances surrounding their detection and rejection as commercially acceptable are different. Most container and closure defects are easier to detect than particulate matter in a pharmaceutical-type product. Guidance provided by the Parenteral Drug Association (PDA) and the U.S. Food and Drug Administration (FDA) has enabled the creation of clearly defined acceptance criteria and disposition for each type of container and closure defect. On Aug. 1, 2014, the United States Pharmacopeia (USP) released an inspection program as described in Chapter 790, hereby incorporated by reference in its entirety, for detection of particulate matter for products that are injectable for parenteral administration.

Regulations require pharmaceutical-type products intended for injection or ophthalmic use to be sterile and free of particles that could harm a patient. With respect to sterile drug products, only microbial assays can confirm sterility of the drug products. With respect to the drug products being free of particles that could harm a patient, this standard is met by incorporating two Regulatory particulate matter determination methods. The first determination method is in accordance with USP Chapter 790, which requires 100% inspection of every drug container in the lot and the removal of any defective units containing visible size particles, before the batch is released for patient use and is deemed commercially acceptable. For example, Chapter 790 of the USP sets forth the expectation for injectable and ophthalmic products to be "essentially free" of visible particulate matter. This expectation, however, is based on human visual acuity, which is subjective and can be affected by many variables. The second determination method is in accordance with testing methodology and acceptance criteria for sub-visible particles in USP Chapters 788, 789 and 1788.

SUMMARY

An exemplary embodiment of a surrogate challenge set may comprise a plurality of containers containing a fluid, wherein at least one of the containers is seeded with particulate matter; and reference probability-of-detection (POD) data for the at least one container containing the particulate matter. The reference POD data may be obtained with criteria that define a pre-determined light intensity, criteria to establish the confidence of the POD values, a range of probabilities that result from the confidence levels and a pre-determined number of inspections for a given seeded container that contains particulate matter.

An exemplary embodiment of a method of making a surrogate challenge set may comprise: disposing particulate matter in at least one of a plurality of containers comprising a fluid; and including reference probability-of-detection (POD) data for the at least one container containing the particulate matter in the challenge set. The method may further comprise generating the probability-of-detection (POD) data for the at least one container containing the particulate matter by inspecting, multiple times, each of the plurality of containers containing the particulate matter; recording, for each inspection, whether or not the particulate matter was detected; and developing a statistical likelihood of detecting the particulate matter. The reference POD data may be obtained with criteria that define a pre-determined light intensity, criteria to establish the confidence of the POD values, a range of probabilities that result from the confidence levels and a predetermined number of inspections for a given seeded container that contains particulate matter.

An exemplary embodiment of a method of using a surrogate challenge comprising a plurality of containers containing a fluid, wherein at least one of the containers contains particulate matter; and reference probability-of-detection (POD) data for the at least one container containing the particulate matter; may comprise: generating comparative probability-of-detection (POD) data for the at least one container containing the particulate matter; and comparing the comparative probability-of-detection (POD) data for the at least one container containing the particulate matter against the reference probability-of-detection (POD) data for the at least one container containing the particulate matter. The generating step may comprise inspecting, multiple times, each of the plurality of containers; recording, for each inspection, whether or not the particulate matter was detected; and developing a statistical likelihood of detecting the particulate matter. The reference POD data and comparative POD data may be obtained with criteria that define a pre-determined light intensity, criteria to establish the confidence of the POD values, a range of probabilities that result from the confidence levels and a predetermined number of inspections for a given seeded container that contains particulate matter.

For each of the aforementioned exemplary embodiments, the fluid may be water containing at least about 0.5 wt % of a preservative, such as benzyl alcohol and about 10% to about 20% of the containers contain particulate matter.

For each of the aforementioned exemplary embodiments, the containers may be pharmaceutically acceptable containers selected from the group consisting of vials, bottles, syringes, ampules and intravenous bags; and the containers may be made of glass or plastic.

For each of the aforementioned exemplary embodiments, the particulate matter may consist of a single particle and have a particle size of at least about 50 μm. The particulate matter, typically found in manufacturing processes, may be any one of glass, rubber, metal, fibers or combinations thereof. For example, the particulate matter may be spheres of polystryrene latex.

For each of the aforementioned exemplary embodiments, the challenge set has a usable shelf-life of at least about one year.

DETAILED DESCRIPTION

Figure 1:
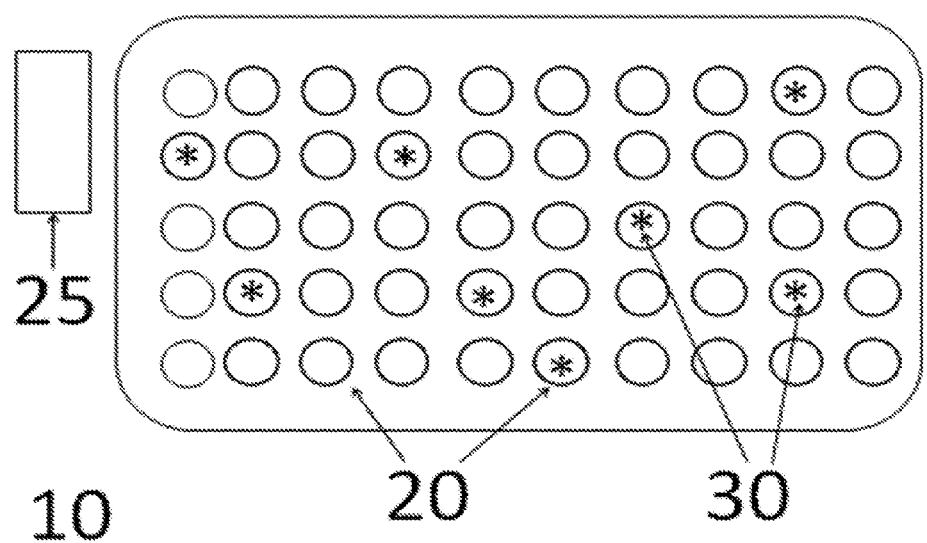
FIG. 1 shows a top view of an exemplary challenge set having a plurality of containers with between 10-20% of the containers containing particulate matter.

Sterile injectable and ophthalmic drugs can be prepared in a manner that is designed to exclude particulate matter. This can be satisfied by testing for sub-visual particles in the laboratory and 100% inspection of all containers for the presence of visible particles. Inspection for visible particles is performed in the operations area using one of three methods. Manual inspection is based on human visual acuity, the ability of the inspector to discern between conforming and non-conforming containers, and the ability to remove non-conforming units. Semi-automated inspection is a variation of manual inspection, in which a roller conveyor or common physical 'clip' or 'clamp' holds a group of more than one container, handles the containers and presents the containers to the human inspector. Fully automated inspection systems perform handling, inspection, and rejection of containers. All inspection methods can meet, for example, the compendial requirement for sterile drug product to be "essentially free" of visible particulates, as described in *Pharmacopeial Forum Online*, USP 790, May 1, 2012, hereby incorporated by reference in its entirety, and in USP 790, Aug. 1, 2014.

Given the random occurrence of particles within the batch, visual detection of a particle in an individual container is probabilistic. The probability-of-detection (POD) is described as a ratio of the number of times a contaminant is detected in a seeded container divided by the total number of inspections of the same container by a given inspector or inspection system. The POD for a specific particle is affected by many variables that include product attributes, container size and shape, particle composition and size, refractive index of a specific particle, refractive index of a solution containing the specific particle, the type of light source, the illuminated light intensity, the manual manipulation of the container to cause fluid and particle movement, the visual acuity of the inspector, and the inspection capability. A challenge set may be a useful tool to assess the probability of particle detection in a product, and it may also be used to evaluate detection of container/closure defects. While the importance of a well-designed challenge set is not always recognized or understood, it serves as the cornerstone for qualification and/or validation of inspection methods.

Challenge sets are useful in establishing the detection, or the probability of detection of visible particulate matter, whether these methods involve manual inspection, semi-automated inspection or fully automated inspection. They can be used to train inspectors, qualify and re-qualify inspectors, and establish a performance baseline. The baseline can be used to validate alternate inspection methods, evaluate changes to the inspection process, or perform pre-production functionality testing of an inspection system. The size and scope of a challenge set may expand with experience, and useful information that is gained can lead to process improvements. Challenge sets provide a measurable link between the probability-of-detection (POD) for various particle types and sizes. All challenge sets contain a subset of defect-free containers and a subset of containers having a known defect. The challenge set, in combination with pre-determined acceptance criteria and a sound inspection strategy, enables qualification/validation of inspection methods designed to differentiate between defect-free versus defective containers.

The principles for the design and use of a challenge set apply to manual qualification and validation of automated systems for particle detection or container/closure defect detection. During inspection of commercial product, container/closure defect and particulate inspection may be performed in a one- or two-step process. Inspection for container/closure defects involves slow rotation of the container to examine all surfaces, while particulate detection requires a greater rotation speed to put particles in motion, which enhances the probability of detection. Maintaining separate data and calculations for each type of defect can be beneficial to gain an understanding of both aspects of inspection.

It can be beneficial that the particles in the challenge set are similar types of materials and have similar particle attributes as those found in the commercial product and that the challenge set contains a sufficient number of defective units to provide an accurate assessment of the capability of the inspection process and probability-of-detection (POD). Regulatory guidance requires the use of challenge sets for qualifying human inspectors and automated systems utilized in visual inspection for detection of visible particles. Thus, there exists a need for more harmonized guidance for detection of "visible particles" for products such as injectable and ophthalmic products. Surrogate challenge sets may provide such guidance.

Several factors can be considered when designing a challenge set, as the probability-of-detection (POD) of particulate matter for manual inspection can be subjective. Factors that contribute to, and affect, the POD can, for example, include: 1) product attributes (such as the container used and filling liquid); 2) particle attributes (e.g., types of particles, properties of particles, etc.); 3) technique attributes (e.g., mixing, observing); 4) inspection equipment attributes (e.g., lighting); 5) training and qualification of inspectors; and 6) monitoring and understanding qualification results. Often more than one particle type and size may be required to provide an improved confidence level in assessing the POD.

Comparative challenge sets do not come with probability-of-detection (POD) data for each container in the challenge set. The challenge sets described herein, also known as "surrogate challenge sets," come provided with probability-of-detection (POD) data (e.g., reference POD data) for each container in the surrogate challenge set. Each reference POD is created based on and/or provided with: 1) multiple inspections carried out at a pre-defined light intensity; 2) using trained and qualified inspectors; 3) following a well-defined and validated procedure; 4) each parameter being measured and documented; and 5) a certificate of analysis provided with traceability. Ideally, the surrogate challenge sets and corresponding POD data described herein are fabricated with conditions (e.g., lighting, sample manipulation etc.) as close as possible to the customer's inspection process.

The benefits of surrogate challenge sets that include reference POD data for each container in the challenge set are many, and include: 1) immediate use (for example, no diversion of resources); 2) lower overall cost of product inspections (for example, no collection of POD data as it is already provided; 3) very tightly held constraints for inspections; and 4) documentation which describes how the reference POD was determined (e.g., inspectors, training, qualification, etc.). For example, the reference POD data may be obtained using at least 3 inspectors with at least about 30 inspections per inspector per container of the surrogate challenge set.

The surrogate challenge sets described herein may be off-the-shelf or custom. An off-the-shelf surrogate challenge set is not customized to any specific manufacturing process and may be prepared with particulate matter commonly found in pharmaceutical or biotechnological products. Such sets can be used as a starter set or a training set. A custom surrogate challenge set is designed for a specific customer/product, whereby the parameters and details of the inspection process preferably mimic as close as possible the criteria and characteristics of the drug manufacturer's inspection process. These criteria include the lighting of the process, the inspector's specific container manipulation/movement, the training and qualification processes for the inspectors, the pacing of the inspections, etc.

The surrogate challenge set may comprise a plurality of containers containing a fluid, wherein at least one of the containers contains particulate matter; and reference probability-of-detection (POD) data for the at least one container containing the particulate matter. FIG. 1 shows an embodiment of an exemplary surrogate challenge set 10 described herein. The surrogate challenge set 10 shown in FIG. 1 includes a plurality of containers 20 (e.g., 50 containers) containing fluid, whereby between about 10% to about 20% of the containers 20 contain particulate matter 30. Reference probability-of-detection (POD) data 25 for the containers 20 containing particulate matter 30 may be included in the challenge set 10.

The number of containers in the surrogate challenge set is not particularly limited, so long as there are a sufficient number of containers that represent the range of particle types and sizes required to provide a statistical assessment of process capability. The experimental design and end-uses of the challenge set can determine the number of containers in the set. For example, the number of containers in the surrogate challenge set may be between about 1 and about 500, for example, between about 50 and about 400, for example, between about 100 and about 250. The number of seeded containers in the surrogate challenge set is also not particularly limited. Preferably, the challenge set comprises at least 1 seeded container for every 100 total containers (e.g., 1 seeded container in combination with 99 non-seeded containers), or at least 5 seeded containers for every 100 total containers (e.g., 5 seeded container in combination with 95 non-seeded containers), or at least 10 seeded containers for every 100 total containers (e.g., 10 seeded container in combination with 90 non-seeded containers), or at least 15 seeded containers for every 100 total containers (e.g., 15 seeded container in combination with 85 non-seeded containers).

Container configuration and the material of construction can affect the ability to detect particles. The types of containers used are not particularly limited, so long as the containers closely mimic those of an actual production process, wherein a product is disposed inside the container. For example, the containers may be pharmaceutically-acceptable containers selected from the group consisting of vials, bottles, syringes, ampules and intravenous bags. The containers may be single compartment or multi-compartment. For example, the containers are made of glass or plastic. For example, the containers are colorless and transparent, but may also be colored and translucent. The size of the containers is not particularly limited and may be from between about 0.05 mL to about 1000 mL, or at least about 2 mL, or at least about 5 mL, or at least about 10 mL or at least about 25 mL, or at least about 50 mL.

The fluid that may be contained in the containers of the surrogate challenge set is not particularly limited, so long as the fluid closely mimics the fluid of an actual production process. The fluids may be aqueous based, drug-product based or placebo based (if drug-product solution is toxic). The fluid characteristics of its refractive index, viscosity, turbidity and opalescence can be considered as part of the understanding of the characteristics of the challenge set, when the particles sizes to be utilized are determined. These parameters can have a bearing on the POD for a given size particle. For water based challenge sets, these parameters are not required, but for placebo or drug product related challenge sets, each of the parameters will have an effect on the POD. For example, a number of injectable pharmaceutical formulations use water as a dispersion medium. Thus, the fluid contained in the containers of the surrogate challenge set may be water. For example, the containers are substantially filled with the fluid. Since it takes a considerable amount of time and resources to construct a surrogate challenge set, it is important that the surrogate challenge set be stable over long periods of time and demonstrate reproducibility of results. Thus, the fluid contained in the containers of the surrogate challenge set may comprise a preservative. For example, the preservative is present in the fluid from about 0.1 weight % (wt %) to about 10 wt %. For example, the preservative is present from about 0.25 wt % to about 5 wt %, or from about 0.5 wt % to about 1 wt %. For example, the fluid comprises at least about 0.5 wt % of preservative. The preservative itself is not particularly limited and can be benzyl alcohol or ethylenediaminetetraacetic acid (EDTA). The combination of the fluid and preservative can lead to a shelf life of the surrogate challenge set of at least about 1 year, for example, at least about 2 years, for example, at least about 3 years, or about 3 years to about 5 years.

The particulate matter contained in the containers of the surrogate challenge set is not particularly limited, so long as the particulate matter closely mimics the particulate matter that may contaminate or end up in a container of an actual production process. In other words, the particulate matter may be: a) extrinsic to a production process (e.g., from the environment, such as hair or dirt); b) intrinsic to a production process (e.g., from the container or production process itself); c) inherent particles such as protein aggregates in biological solutions; or d) simulated from a laboratory process wherein the particulate matter would react in a similar manner as natural particles during spinning and manual inspection.

Regarding intrinsic particulate matter, such matter may be any one of glass, rubber, metal, fibers or combinations thereof. For example, if fibers, the fibers may be natural or synthetic fibers including, but not limited to, cotton, rayon, nylon, polyester, polypropylene, Teflon® fluoropolymer resin, Teflon® fluorinated ethylene propylene, wipers and garments among others. For example, if glass, the glass may be glass spheres, glass shards or glass lamella of the specific product configuration. For example, if rubber, the rubber may be rubber fragments from a rubber stopper, a rubber diaphragm or an "O" ring. For example, if metal, the metal may be stainless steel, such as stainless steel shards from manufacturing or filling equipment. For example, the containers may contain particulate matter in the form of glass spheres, glass shards or rubber particles.

Not every container in the surrogate challenge set will contain particulate matter. For example, prior art challenge sets included about 80% blank containers which do not contain any particles (e.g., containing only the fluid and preservative) while about 20% of the containers are seeded with particulate matter. For example, the surrogate challenge sets described herein have about 1% to about 50% of the containers seeded with particulate matter, for example, about 5% to about 40%, for example, from about 10% to about 30% or from about 10% to about 20% of the containers being seeded with particulate matter.

The particulate matter may be in the form of single or multiple particles. Regarding multiple particles, it has been found that containers containing more than one particle will result in an artificially increased POD. This is due to a multiplying effect of two smaller particles in proximity being detected as one large particle. As a result, the containers that contain particulate matter can contain the particulate matter in the form of a single particle. The size of the particle can be a size that is visible to an inspector having about 20/20 visual acuity, such as at least about 50 μm. Other sizes may be utilized as well, such as a particle size of at least about 75 μm, or at least about 100 μm, or at least about 150 μm, or at least about 200 μm, or at least about 250 μm, or at least about 500 μm. The extraneous contamination has direct effect on POD. Containers should be cleaned such that they have no particles >25 μm to minimize variability in POD seeded containers and to avoid false rejects in blank containers with no seeded particles.

The reference POD data may be obtained at a pre-determined light intensity, such as each container (whether or not it contains particulate matter to be detected) being inspected under a light intensity of 100 foot candles, 250 foot candles or 500 foot candles. The reference POD data may be obtained at a pre-determined light intensity in a range of 100 foot candles to 500 foot candles, or any other pre-defined light intensity range, such as a light intensity that is about 500 foot candles or higher for special types of containers such as amber containers. A pre-defined light intensity for each container inspection helps ensure consistency of the conditions used to determine the reference POD.

TABLE 1

Examples of Inspection Scenarios Using Surrogate Challenge Sets

| Light Level (fc) | Number of inspections per Surrogate Set (per inspector) | | Container Inspection Time per background (sec) |
| --- | --- | --- | --- |
| 100 | 10 | 20 | 30 | 10 |
| 250 | 10 | 20 | 30 | 10 |
| 500 | 10 | 20 | 30 | 10 |
| 100 | 10 | 20 | 30 | 20 |
| 250 | 10 | 20 | 30 | 20 |
| 500 | 10 | 20 | 30 | 20 |
| 100 | 10 | 20 | 30 | 30 |
| 250 | 10 | 20 | 30 | 30 |
| 500 | 10 | 20 | 30 | 30 |

The surrogate challenge set may be divided into three subsets based upon the reference POD, which is calculated by a minimum of 10-20 inspections, preferably 30 inspections or more. The containers are placed into one of three subsets based on their reference POD: 1) The Accept subset; 2) the Grey Zone subset; and 3) the Reject subset. In the Accept subset, the containers have a rejection probability ranging from 0 to about 0.3. In the Grey Zone subset, the containers have a rejection probability ranging from about 0.3 to about 0.7. The containers that fall into the Grey Zone subset are not true rejects, but are containers that are sensitive to subtle changes in the inspection process. They provide security that the reject containers are detected. In the Reject subset, the containers have a rejection probability ranging from about 0.7 to about 1.0.

TABLE 2

Confidence Limits (90%) for PODs of Surrogate Challenge Sets
90% Exact Binomial Confidence Limits on Observed POD's

| Probability of Detection (POD) demonstrated by an individual Inspector | Number of inspections performed by an individual Inspector on an individual particle-containing vial in a Surrogate Set | | | |
| --- | --- | --- | --- | --- |
| | 10 | 20 | 30 | 50 |
| 90% | 60.6% to 99.5% | 71.7% to 98.2% | 76.1% to 97.2% | 80.1% to 96.0% |
| 80% | 49.3% to 96.3% | 59.9% to 92.9% | 64.3% to 90.9% | 68.4% to 88.7% |
| 60% | 30.4% to 85.0% | 39.4% to 78.3% | 43.4% to 75.0% | 47.4% to 71.7% |
| 40% | 15.0% to 69.6% | 21.7% to 60.6% | 25.0% to 56.6% | 28.3% to 52.6% |
| 20% | 3.7% to 50.7% | 7.1% to 40.1% | 9.1% to 35.7% | 11.3% to 31.6% |
| 10% | 0.5% to 39.4% | 1.8% to 28.3% | 2.8% to 23.9% | 4.0% to 19.9% |

The surrogate challenge set may be inspected multiple times to develop a statistical reference POD for each container in the set. Clearly, confidence in the reference POD increases with the number and/or length of inspections and/or increased light intensity. At some point practicality limits the number of manual inspections that can be performed. Table 1 shows scenarios of how confidence may be increased using the surrogate challenge sets, wherein the light intensity (in foot candles), the number of inspections per surrogate set (per inspector) and container inspection time per background (in seconds) are listed. For example, the time taken to inspect each container is less than about 30 seconds, or less than about 25 seconds, or less than about 20 seconds, or less than about 15 seconds, or less than about 10 seconds, or less than about 5 seconds, or less than about 3 seconds.

In Table 2, confidence limits may be established, for example, if an inspector performs 30 inspections of a seeded (e.g., particle-containing) container. If the POD is calculated based upon those 30 inspections to be 80%, one could be 90% positive that if the inspection were to have been carried out, for example, with 30 million inspections instead of 30 inspections, the POD calculated based upon 30 million would be somewhere in the interval between 64.3% and 90.9%. Thus, 90% confidence limits are the extreme ends of the interval in which one can expect (with 90% confidence) to find the "true" POD for the combination of a given inspector, a given particle-containing vial from a surrogate set, and a given inspection process. Because such an interval is based upon a finite sample, it may be possible that the confidence interval does not contain the "true" value. In Table 2, the calculated limits have a 10% chance (100%-90%) of not containing the "true" value.

TABLE 3

Confidence Limits (95%) for PODs of Surrogate Challenge Sets
95% Exact Binomial Confidence Limits on Observed POD's

| Probability of Detection (POD) demonstrated by an individual Inspector | Number of inspections performed by an individual Inspector on an individual particle-containing vial in a Surrogate Set | | | |
|---|---|---|---|---|
| | 10 | 20 | 30 | 50 |
| 90% | 55.5% to 99.7% | 68.3% to 98.8% | 73.5% to 97.9% | 78.2% to 96.7% |
| 80% | 44.4% to 97.5% | 56.3% to 94.3% | 61.4% to 92.3% | 66.3% to 90.0% |
| 60% | 26.2% to 87.8% | 36.1% to 80.9% | 40.6% to 77.3% | 45.2% to 73.6% |
| 40% | 12.2% to 73.8% | 19.1% to 63.9% | 22.7% to 59.4% | 26.4% to 54.8% |
| 20% | 2.5% to 55.6% | 5.7% to 43.7% | 7.7% to 38.6% | 10.0% to 33.7% |
| 10% | 0.3% to 44.5% | 1.2% to 31.7% | 2.1% to 26.5% | 3.3% to 21.8% |

In Table 3, confidence limits may be established, for example, if an inspector performs 30 inspections of a seeded (e.g., particle-containing) container. If the POD is calculated based upon those 30 inspections to be 80%, one could be 95% positive that if the inspection were to have been carried out, for example, with 30 million inspections instead of 30 inspections, the POD calculated based upon 30 million would be somewhere in the interval between 61.4% and 92.3%. Thus, 95% confidence limits are the extreme ends of the interval in which one can expect (with 95% confidence) to find the "true" POD for the combination of a given inspector, a given particle-containing vial from a surrogate set, and a given inspection process. Because such an interval is based upon a finite sample, it may be possible that the confidence interval does not contain the "true" value. In Table 2, the calculated limits have a 5% chance (100%-95%) of not containing the "true" value.

Figure 2:
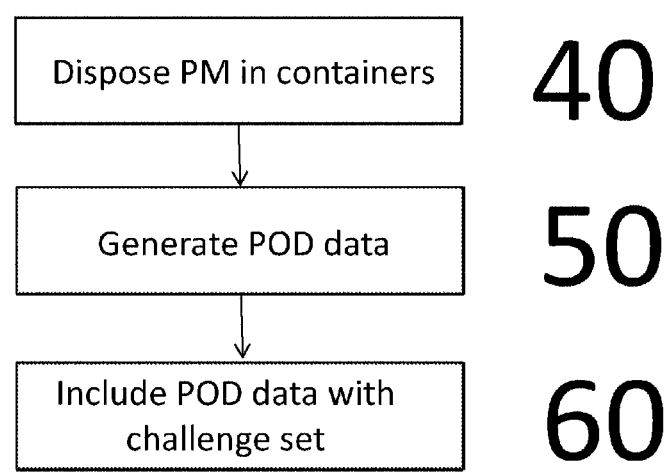
FIG. 2 shows a flow diagram for an exemplary method of making a challenge set.

Methods of making the surrogate challenge sets described herein are not particularly limited. FIG. 2 shows an exemplary method of making surrogate challenge sets described herein, which may comprise: a step 40 of disposing or seeding particulate matter in at least one of a plurality of containers comprising a fluid; a step 50 of generating the reference probability-of-detection (POD) data for the at least one container containing the particulate matter; and a step 60 of including the reference probability-of-detection (POD) data for the at least one container containing the particulate matter in the surrogate challenge set. For example, the method may include ascertaining at least one condition (such as light intensity as light intensity effects POD) in a first environment (such as a first viewing station), adjusting at least one condition (such as light intensity) in a second environment (such as a second viewing station) to more closely correspond to the at least one condition in the first environment, and making the challenge set in the second environment after adjustment of the at least one condition. For example, the challenge set may be produced in the second environment under the same or substantially the same condition (such as light intensity) as in the first environment. The first environment may be, for example, the inspection area of a drug production line. The second environment may be, for example, the inspection area of a producing line for producing the challenge sets.

For example, ascertaining the light intensity (which effects POD) may include measuring light intensity at one or more locations (such as 10 to 30 locations, such as 18 locations) in a viewing station for inspecting the containers in the first environment. The locations at which the light intensity are measured may be located in the space in which an inspector is likely to hold the containers during inspection. Such locations may depend on, for example, the size of the containers. Such locations may be, for example, 6 to 22 inches, for example, about 14 inches, from the eyes of the inspector when the inspector is holding the container in a position for inspection. Such locations can be, for example, 4 to 12 inches from a light source of the viewing station. For example, the light intensity at one or more of the same locations in a viewing station in the second environment may then be adjusted to more closely correspond to the first environment. The intent may be, for example, to measure the end user's light intensity for routine inspection and duplicate this light intensity in the laboratory to obtain the POD after the set has been created and will be inspected. The characteristics of the manipulation or technique utilized to cause the particle of interest to be put into motion (for detection) of the container by the end user may be duplicated since manipulation has an effect on the POD.

For the disposing or seeding of the particulate matter step, the fluid may be added to the containers prior to the addition of the particulate matter or vice versa. The fluid is added to the containers from a stock solution. In an exemplary embodiment, the fluid is free of extraneous particulate matter that is ≥25 μm. The particulate matter may be disposed or seeded in the containers manually or by an automated process. The particulate matter may be obtained from a bulk material. Razors, scissors or other cutting or shaving instruments may be used to cut or shave the bulk material into desirable sizes. In some instances, smashing or pulverizing may be more practical than cutting or shaving. In some instances, the particulate matter may be obtained commercially in the desired size, with no further processing needed. The particulate matter may be transferred, disposed or seeded in the containers with, for example, tweezers or a needle, such as a pithing needle, or any other equipment designed to manipulate very small (e.g., 1-1000 micron) particles.

Generating the reference POD data may comprise: 1) inspecting, multiple times, each of the plurality of containers; 2) recording, for each inspection, whether or not the particulate matter was detected; and 3) developing a statistical likelihood of detecting the particulate matter. Including the reference probability-of-detection (POD) data for the at least one container containing the particulate matter in the surrogate challenge set may comprise generating the reference POD data (as described above) and providing this reference POD data with the surrogate challenge set.

The surrogate challenge sets described herein have many industrial uses and are particularly useful for qualifying (e.g., testing) human inspectors or automated systems. A method of using a surrogate challenge set described herein may comprise: generating comparative probability-of-detection (POD) data for the at least one container containing the particulate matter; and comparing the comparative probability-of-detection (POD) data for the at least one container containing the particulate matter against the reference probability-of-detection (POD) data for the at least one container containing the particulate matter. In other words, the comparative POD data may be generated by the inspectors who perform their own POD analysis of the surrogate challenge set. To see the accuracy of the inspectors, the comparative POD data may be compared to the reference POD data that may be included with the surrogate challenge set.

Generating the comparative POD data may comprise: 1) inspecting, multiple times, each of the plurality of containers; 2) recording, for each inspection, whether or not the particulate matter was detected; and 3) developing a statistical likelihood of detecting the particulate matter. Methods, techniques and conditions under which the comparative POD data is generated can mimic as closely as possible the conditions under which the reference POD data was generated or vice versa. For example, both the comparative POD data and the reference POD data may be obtained under the same, pre-defined light intensity using a similar fluid and similar particulate matter.

For the methods of making and using the surrogate challenge sets, as well as the surrogate challenge sets, a visual inspection workstation according to "General Visual Inspection Bench Parameters" R. Cherris, 2009-2013, *Bridge Associates International*, hereby incorporated by reference in its entirety, may be used for inspecting the containers. For generating the data, testing protocols in accordance with the methods described in *European Medicines Agency* (EMEA) Chapter 2.9.18 to 2.9.20; 01/2008: 20920, hereby incorporated by reference in its entirety, may be used.

Such methods of using a surrogate challenge set as described herein may lead to improved annual qualification comparisons, improved Reject/Grey Zone definitions and improved measure of small changes to inspection.

Although the present invention has been described in connection with exemplary embodiments thereof, it will be appreciated by those skilled in the art that additions, deletions, modifications, and substitutions not specifically described can be made without departing from the spirit and scope of the invention as defined in the appended claims.

What is claimed is:

1. A challenge set comprising:
    a plurality of containers containing a fluid, wherein about 10% to about 20% of the containers contains particulate matter; and
    reference probability-of-detection (POD) data for the at least one container containing the particulate matter.

2. The challenge set of claim 1, wherein the fluid is water containing at least about 0.5 wt % of a preservative.

3. The challenge set of claim 2, wherein the preservative is benzyl alcohol or EDTA.

4. The challenge set of claim 1, wherein the containers are pharmaceutically acceptable containers selected from the group consisting of vials, bottles, syringes, ampules and intravenous bags; and the containers are made of glass or plastic.

5. The challenge set of claim 1, wherein the particulate matter consists of a single particle.

6. The challenge set of claim 1, wherein the particulate matter has a particle size of at least about 50 µm.

7. The challenge set of claim 1, having a usable shelf-life of at least about 3 years.

8. The challenge set of claim 1, wherein the particulate matter is glass, rubber, metal, fibers or combinations thereof.

9. The challenge set of claim 1, wherein the reference probability-of-detection (POD) data for the at least one container containing particulate matter is obtained at a pre-defined light intensity.

10. The challenge set of claim 1, wherein the fluid is aqueous based, drug product based or placebo based.

11. A method of making a challenge set comprising:
    disposing particulate matter in about 10% to about 20% of a plurality of containers comprising a fluid; and
    including reference probability-of-detection (POD) data for the at least one container containing the particulate matter in the challenge set.

12. The method of claim 11, further comprising generating the probability-of-detection (POD) data for the at least one container containing the particulate matter.

13. The method of claim 12, wherein generating the reference probability-of-detection (POD) data for the at least one container containing the particulate matter comprises:
    inspecting, multiple times, each of the containers containing the particulate matter;
    recording, for each inspection, whether or not the particulate matter was detected; and
    developing a statistical likelihood of detecting the particulate matter.

14. The method of claim 12, wherein generating the probability-of-detection (POD) data for the at least one container containing particulate matter is carried out at a pre-defined light intensity.

15. The method of claim 11, wherein the fluid is water containing at least about 0.5 wt % of a preservative.

16. The method of claim 15, wherein the preservative is benzyl alcohol or EDTA.

17. The method of claim 11, wherein the containers are pharmaceutically acceptable containers selected from the group consisting of vials, bottles, syringes, ampules and intravenous bags; and the containers are made of glass or plastic.

18. The method of claim 11, wherein the particulate matter has a particle size of at least about 50 µm.

19. The method of claim 11, wherein the particulate matter is glass, rubber, metal, fibers or combinations thereof.

20. The method of claim 11, wherein the particulate matter consists of a single particle.

21. The method of claim 11, wherein the fluid is aqueous based, drug product based or placebo based.

22. A method of using a challenge set, the challenge set comprising: a plurality of containers containing a fluid, wherein about 10% to about 20% of the containers contains particulate matter; and reference probability-of-detection (POD) data for the at least one container containing the particulate matter; the method comprising:
    generating comparative probability-of-detection (POD) data for the at least one container containing the particulate matter; and
    comparing the comparative probability-of-detection (POD) data for the at least one container containing the particulate matter against the reference probability-of-detection (POD) data for the at least one container containing the particulate matter;
    wherein generating the comparative probability-of-detection (POD) data for the at least one container containing the particulate matter comprises:
        inspecting, multiple times, each of the containers containing the particulate matter;

recording, for each inspection, whether or not the particulate matter was detected; and developing a statistical likelihood of detecting the particulate matter.

23. The method of claim 22, wherein generating the comparative probability-of-detection (POD) data for the at least one container containing the particulate matter is carried out at a same pre-defined light intensity as the reference probability-of-detection (POD) data for the at least one container containing the particulate matter.

24. The method of claim 22, wherein the fluid is water containing at least about 0.5 wt % of a preservative.

25. The method of claim 24, wherein the preservative is benzyl alcohol or EDTA.

26. The method of claim 22, wherein the containers are pharmaceutically acceptable containers selected from the group consisting of vials, bottles, syringes, ampules and intravenous bags; and the containers are made of glass or plastic.

27. The method of claim 22, wherein the particulate matter has a particle size of at least about 50 µm.

28. The method of claim 22, wherein the particulate matter is glass, rubber, metal, fibers or combinations thereof.

29. The method of claim 22, wherein the particulate matter consists of a single particle.

30. The method of claim 22, wherein the fluid is aqueous based, drug product based or placebo based.

\* \* \* \* \*